United States Patent [19]

Vogel et al.

[11] 4,058,766

[45] Nov. 15, 1977

[54] MULTIPLE-FREQUENCY PERMITTIVITY TESTER

[75] Inventors: Ronald F. Vogel, Bettendorf, Iowa; Robert R. Boldt, Taylor Ridge, Ill.; Kevin D. McKee, Davenport, Iowa; Roy E. Resh, Bettendorf, Iowa; Paul E. West, Davenport, Iowa

[73] Assignee: Agridustrial Electronics, Inc., Bettendorf, Iowa

[21] Appl. No.: 697,858

[22] Filed: June 21, 1976

[51] Int. Cl.² ............................................. G01R 27/26
[52] U.S. Cl. .................................... 324/61 R; 364/481
[58] Field of Search ........................... 324/61 R, 60 R; 235/151.3, 151.31, 151.35

[56] References Cited
U.S. PATENT DOCUMENTS

| 3,496,460 | 2/1970 | Martin .............................. 324/61 R |
| 3,666,621 | 5/1972 | Adams ......................... 235/151.35 X |
| 3,687,802 | 8/1972 | Rummel et al. ............. 235/151.35 X |
| 3,691,457 | 9/1972 | Kriellaars ........................... 324/61 R |
| 3,715,656 | 2/1973 | Hyde et al. ........................ 324/61 R |
| 3,723,865 | 3/1973 | Batey et al. ........................ 324/61 R |

Primary Examiner—Rudolph V. Rolinec
Assistant Examiner—Vincent J. Sunderdick
Attorney, Agent, or Firm—Olson, Trexler, Wolters, Bushnell & Fosse, Ltd.

[57] ABSTRACT

As in prior testers, a capacitive cell in which material is placed to be tested is connected in a voltage divider circuit. However, signal generating means connected to the voltage divider applies voltages at different predetermined frequencies selected for the material being tested, and frequency selective means connected to the cell develop voltages at the applied frequencies having values dependent on the impedance of the filled cell at the respective frequencies. These voltages developed across the cell are applied to a computer that provides an output according to an equation that has been derived statistically from many samples of the material being tested for the substance or quality of the material being measured.

14 Claims, 5 Drawing Figures

MULTIPLE-FREQUENCY PERMITTIVITY TESTER

BACKGROUND OF THE INVENTION

This invention relates to testers using capacitive cells to measure permittivity of materials for determining the content of substances having a distinctive dielectric quality. Testers of this type include those having capacitors shaped like containers or cells into which are placed grains or other particulate materials for measuring their moisture content.

Typically, a type of tester for determining the amount of moisture in a particulate material includes a capacitive cell having an inner cylindrical, insulated electrode of quite small diameter surrounded by an outer electrode of substantially greater diameter. The testers may be portable and adapted for testing materials such as grain in discrete, accurately measured samples poured in the space between the inner and the outer electrodes, or the tester may be permanently installed in a process or handling facility for continually testing a portion of flowing material as it is diverted over a short distance from the main flow to flow downwardly between the electrodes. In either type of tester, the capacitance or impedance of the cell is measured electronically for determining the permittivity of the material, and the reading for permittivity is converted to a reading of moisture either directly on a scale of an output meter or by reference to a conversional table.

Usually, the capacitive cell of the tester is included in a voltage divider, and voltage of repetitive waveform at a single frequency is applied across the voltage divider. The amount of moisture in a material such as grain is determined by measuring the voltage developed across the cell. The readings obtained on a tester of this type are usually valid when the moisture is quite evenly distributed within the kernels of the grain. A different calibration may be required if the moisture is contained in the grain in other ways; for example, the moisture may be contained within the grain not only in a close molecular condition but also it may be contained on the surface of the grain or in capillaries within the kernels either in liquid or in frozen form. Tests show that the permittivity of grain measured in a usual manner at a single frequency appears to be greater for a certain total amount of moisture when a greater portion of the moisture is contained on its surface.

The output readings of testers for measuring permittivity of materials placed in capacitive test cells are affected in various amounts by conditions of the materials such as density and temperature and of composition such as the amount of protein in grain. For temperature correction, temperature sensing devices in contact with the material being tested can control circuits for compensating the output readings of the testers. The amount of materials in the test cells are carefully controlled to maintain density nearly constant. Although the amounts of protein have usually been disregarded in grain moisture testers, changes in output readings with changes in protein in capacitive testers are being investigated not only for increasing the reliability of measurements of moisture but also as possibly providing a quick, reliable means of measuring grain for its amount of protein.

SUMMARY OF THE INVENTION

The present tester includes circuits for developing input voltage waveforms at different predetermined frequencies. Inputs of the different frequencies are applied to a voltage divider including the capacitive testing cell. The outputs derived from the cell are the known quantities to be inserted in an equation that has been developed to provide a quantitative measurement of a characteristic that is dependent on permittivity of the material being tested. For example, when the amount of moisture in a particular grain is to be measured, frequencies and an equation are selected to provide accurate readings according to the amount of moisture in grain, and a computing circuit connected to the output circuit of the capacitive cell is programmed to solve the equation and to provide an output reading for percentage of moisture. In the computation, differences between the readings obtained for certain frequencies are derived, and to these differences are applied constant multipliers that have been derived from previous observation to provide output readings from the computer corrected for different moisture conditions and variations in density. The use of a plurality of frequencies for testing moisture content provides more accurate readings than would be obtained by use of a single frequency in testing grains in which moisture is distributed differently.

A preferred circuit for applying waveforms at different frequencies to the testing cell comprises a square wave generator, a frequency divider including the test cell, and an analog multiplexer. The analog multiplexer applies repeatedly and sequentially voltage of the different frequencies from the frequency divider to the voltage divider. The output developed across the cell in the voltage divider is rectified for providing pulsating direct current to the input of a demultiplexer. The demultiplexer applies the rectified outputs to different filtering and amplifying circuits for the different frequencies. The outputs of the amplifiers are connected to a computer circuit, and the output of the computer circuit is connected to an indicator such as a direct-current meter calibrated in percentage of moisture.

DESCRIPTION OF THE PREFERRED EMBODIMENT

Figure 1:
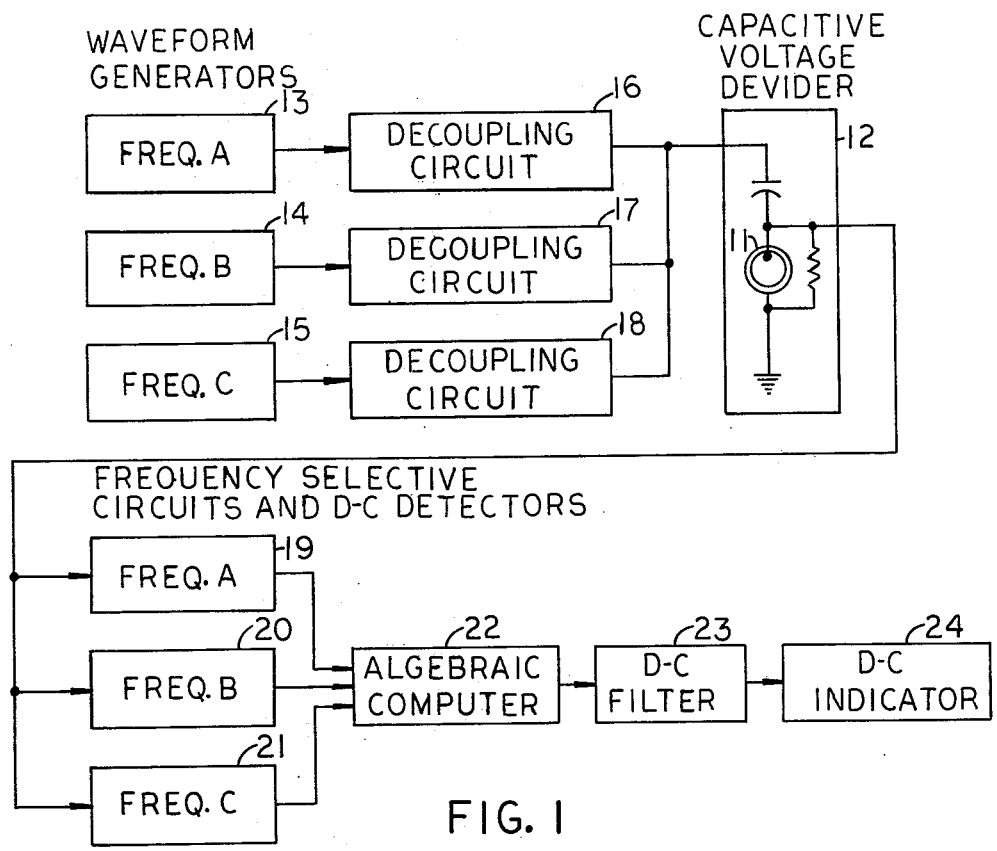
FIG. 1 is a functional block diagram of a multiple-frequency permittivity tester of this invention.

In FIG. 1, a capacitive cell 11 for receiving material to be tested is connected in a voltage divider circuit 12. Basically, the cell 11 is similar to those used in portable grain moisture testers and continuous moisture testers. Capacitive impedance between a central cylindrical electrode and an outer concentric electrode determines the output of the tester and therefore is a function of the dielectric qualities of material placed between the electrodes. The multi-frequency tester also resembles prior testers in that alternating-current voltage is applied across the capacitive voltage divider 12, and voltage developed across the cell 11 is measured as an indication of permittivity of the material contained in the cell 11.

The present tester differs from those using voltage at a single frequency in that voltages at more than one predetermined frequency are applied to the voltage divider 12, and the voltages for the different frequencies developed across the cell 11 are separated and applied to a computer circuit. The voltages represent different points at which permittivity is measured for a sample of material to give effectively the shape of a curve over a wide frequency range. The voltages for application to the voltage divider 12 may be developed at several widely separated frequencies; as shown in a preferred tester of FIG. 1, voltages at three frequencies are developed by waveform generators 13, 14, and 15. Each of the waveform generators 13, 14, and 15 is connected through a respective decoupling circuit 16, 17, or 18 to the capacitive voltage divider 12. Voltages at the different frequencies may be applied to the capacitive voltage divider 12 simultaneously, or the decoupling circuits may include multiplexing circuits for applying the voltages sequentially as described subsequently for FIG. 3.

Frequency selective circuits and direct-current detectors represented by blocks 19, 20, and 21 separate the voltages developed across the capacitive cell 11 at the different frequencies and rectify the voltages for applying them to respective inputs of a computer 22. The computer 22 operates on the voltages according to an equation given below, and direct current from the output of the computer is applied through a filter 23 to an indicator 24.

Figure 2:
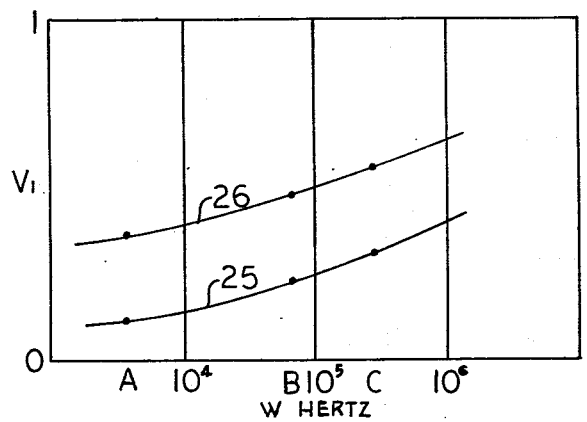
FIG. 2 is a graph showing the output of a capacitive cell over a wide frequency range for two samples of grain having different moisture content.

The conception of the present tester grew from observing curves such as curves 25 and 26 of FIG. 2 for grains having different moisture contents. The curves are plots of voltages developed across a filled test cell at different frequencies of voltages applied to a voltage divider containing the cell. The developed voltages are dependent on the impedance of the filled cell, and the impedance has a capacitive component and a loss component. The permittivity of the material that is being measured is a result of both the capacitive component and the loss component and may be called complex permittivity. Later developments relied on the gathering of statistics of qualities of materials and the utilization of these statistics for selecting frequencies and the appropriate gains for the portions of the circuits operating at these frequencies. The curves of FIG. 2 relate moisture content of corn with frequencies of voltages applied to a voltage divider including a test cell and with the voltage developed across the test cell. Other qualities or characteristics such as density, temperature, and content of protein are considered to be held constant. Although these curves are relatively simple when compared with curves derived from all pertinent variations in qualities, they can be used to explain the general arrangement of the present circuit.

The three frequencies A, B, and C on the horizontal scale of FIG. 2 are derived from the waveform generators 13, 14, and 15 of FIG. 1, and the voltage output shown on the vertical scale is derived from the cell 11. The frequencies A, B, and C are typically approximately 4 kilohertz (Khz), 60 Khz, and 250 Khz, respectively, and on the vertical scale the output voltages are shown as multipliers of a reference voltage applied across the capacitive voltage divider 12. The curve 25 is plotted over a wide frequency range for grains having greater moisture content than that generally desirable for storage or for shipping, and the curve 26 is for grain having a desirable moisture content of about 15 percent.

Typically, prior moisture testers measured the output of a capacitive cell, similar to the cell 11, at a single frequency such as frequency A shown in FIG. 2. The dielectric constant becomes greater as the moisture content increases, and therefore the impedance of the capacitive cell 11 and the voltage measured across it decreases as the moisture content increases. The readings are dependent on the density of the grain, and when using portable testers, the testers have to be filled carefully to obtain the same amount of packing and density in consecutive samples. Special circuits and careful control of the flow of materials are required in continuous moisture testing systems having constant flow of materials to be tested through the capacitive cell.

The slopes or first derivatives for different curves similar to the curves 25 and 26 have been found to have distinct values for the different moisture contents of a material. The derivatives are quite independent of variations in density but are found to vary somewhat according to the way moisture is associated with the material that is being tested. Particularly, materials having substantial moisture on their surfaces appear according to the reading across the capacitive cell 11 to have greater moisture content than they actually have. The error showing greater moisture content is more pronounced when the frequency of the input voltage to the cell is low. For example, the point plotted for frequency A on the curve 25 is somewhat closer to the zero reading than it is expected to be in comparison with the position of the point plotted for the same frequency on the curve 26. The points on curve 25 at the much higher frequencies B and C are more nearly what they would be if the moisture were associated inside the kernels of the grain. A comparison of actual quantities for moisture content and the readings for obtaining curves corresponding to those of FIG. 2 show that the measurement of the slope of the curves would be desirable to help eliminate the errors caused by varying densities, and that a correction for eliminating errors caused by the way in which moisture is contained in the material would be desirable. Through observation of the test results and analysis by the use of a computer, the following equation has been derived:

$V_o = (-V_c + K_1 V_b)(K_2 - K_3 V_a)$ where:

$V_o$ = output voltage from the analog computing network $V_c$ = peak voltage at the output of the capacitive cell 11 at 266 Khz, $V_b$ = peak voltage at 66.5 Khz, and $V_a$ = peak voltage at 4.15 Khz.

$K_1$, $K_2$, and $K_3$ are determined by taking readings on materials of known moisture content by applying the mathematical process of least squares regression. In a typical tester, the constants for measuring moisture content of corn are:

$K_1 = 1.82, K_2 = 1.57,$ and $K_3 = 0.0836.$

The value of $V_o$ is largely determined by the slope of a curve such as curve 25 of FIG. 2 between the readings for the frequencies B and C. For curves such as curve 25 representing materials with quite high moisture content, the slope will be a little greater than would be expected in comparison with the materials having lower moisture content and less moisture contained on the surface of the particles. As described above, the reading at frequency A is affected more by the high moisture content than the readings for the higher frequencies. The constants $K_2$, and $K_3$ are chosen from analysis of tests data to provide the required multiplier for correcting the expression $-V_c + K_1 V_b$ that has been derived for the slope of the curve at the higher frequencies. The computer circuits shown in FIG. 3 provide the necessary addition and multiplication for solving the equation.

Upon determining the form of the equation, accurate output readings can be obtained by selecting both suitable frequencies at which output voltages of the cell are obtained and multiplier constants for use with these voltages. These values for the equation are determined by collecting data from many samples and by using a mathematical method such as least squares regression to determine suitable constants for the equation. For example, in determining moisture content of corn, the samples of corn from which readings are to be obtained must be classified according to known contents of moisture. The samples must also include all other variables such as oil content and different ways of association of moisture that might be expected during normal use of the tester that is to be developed. Frequencies and constants are then selected to provide output readings independent of all variables except the one that is being measured. If content of protein rather than moisture is to be determined, then the frequencies and constants are selected to make output curves dependent on protein and independent of other variables.

Figure 3:
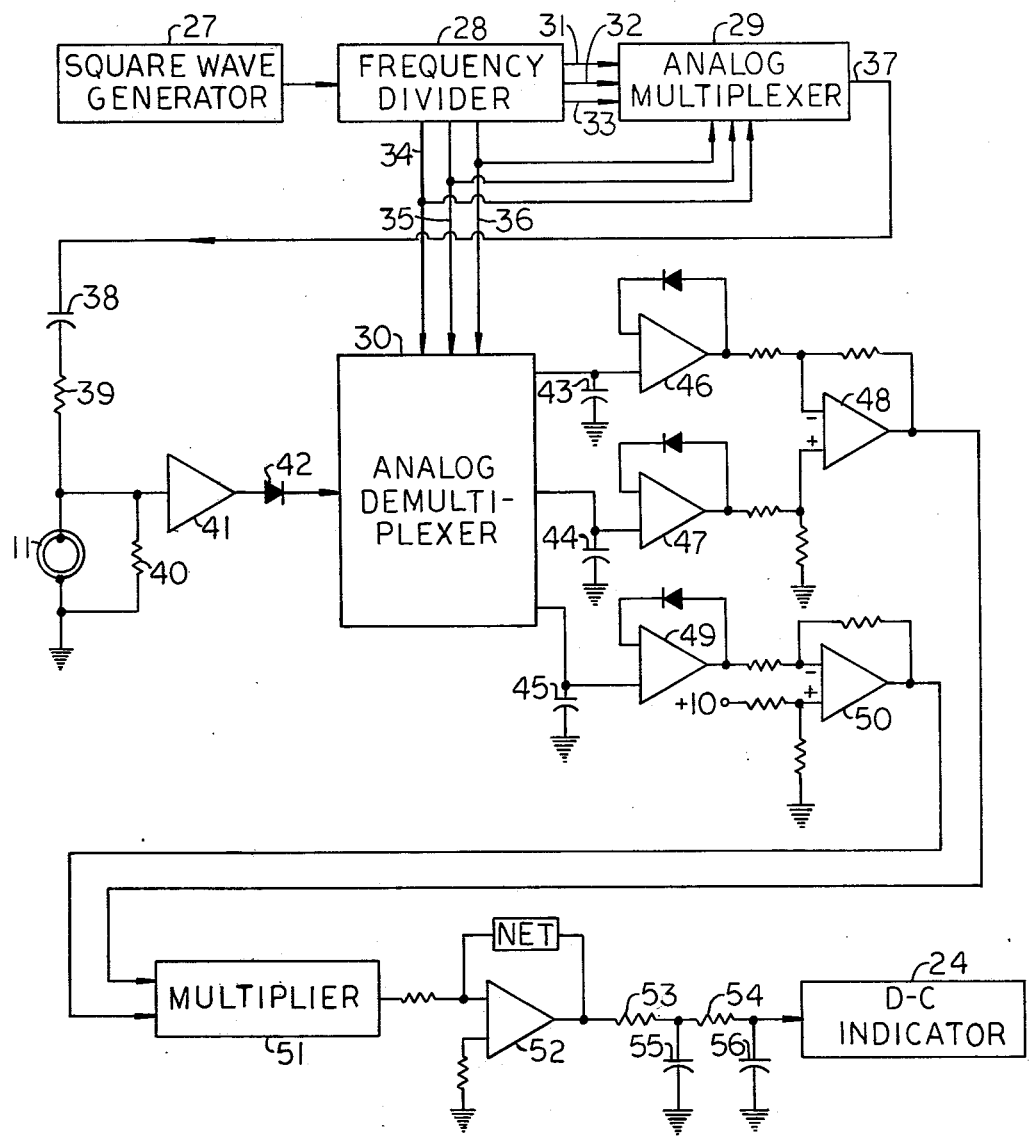
FIG. 3 is a block diagram of a multiple-frequency permittivity tester using multiplexer circuits.

A preferred grain moisture tester of FIG. 3 performs the functions of FIG. 1 to solve the equation described above. A square wave generator 27 and a frequency divider 28 apply signal at the three frequencies A, B, and C of FIG. 1 to a voltage divider circuit containing the capacitive cell 11. Multiplexers 29 and 30 are used to apply signal of the three frequencies sequentially to the cell 11 and to derive respective output voltages for application to a computer circuit.

The output of the square wave generator 27 is connected to the input of the frequency divider 28. In a typical tester, the square wave generator 27 has a fundamental frequency of 1064 Khz. The frequency divider 28 comprises two 7-stage binary counters; each counter may be a RCA model number CD4024A counter. The output of the seventh stage of one of the counters is connected to the input of the first stage of the other counter to provide 14 cascade stages. The three frequencies of the signal applied to the test cell 11 are 266 Khz derived at the output of the second stage of the first binary counter, 66.5 Khz taken from the fourth stage of the first counter, and 4.156 Khz taken from the output of the first stage of the second counter. These frequencies and values of components given below are particularly suitable for measuring the amount of moisture in corn.

Signals at these frequencies are applied through respective conductors 31, 32, and 33 to switching circuits of the analog multiplexer 29. Control signals for switching the multiplexers 29 and 30 are applied from the frequency divider through conductors 34, 35, and 36. Each of the analog multiplexers 29 and 30 may be an RCA Model No. CD4051AD. Because of its function, the multiplexer 30 is labeled a demultiplexer. Each of these multiplexers has eight channels, but according to FIG. 3, only three of the channels are used. When only three or four channels are used, one of the control conductors, for example conductor 34, need not be connected to an output of the frequency divider 28 and can be connected to a source of constant voltage. To provide successive operation of switches for only these channels, the outputs of the sixth and seventh stages of the second frequency counter are connected through the conductors 35 and 36 for supplying signal at frequencies of 129.8 Hz and 64.94 Hz to respective control circuits of both the analog multiplexer 29 and the analog demultiplexer 30. The combination of the two wave forms having a frequency ratio of 2:1 provides required three negative pulses for operating successively the three channels of both the multiplexer 29 and the demultiplexer 30, the corresponding channels being operated simultaneously.

Operation of the multiplexer 29 applies signal in sequence from the conductors 31, 32, and 33 through the switching circuits of the multiplexer 29 to the conductor 37 that is connected between the output of the multiplexer 29 and the voltage divider containing the capacitive cell 11. The voltage divider comprises a capacitor 38 and a resistor 39 connected in series with the capacitive cell 11 and a resistor 40 shunting the capacitive cell. For use with a typical cell as described in U.S. Pat. No. 3,760,267 issued to D. Michael Williams on Sept. 18, 1973, the value of the capacitor 38 is 0.33 microfarad, and the values of resistors 39 and 40 are 57,600 ohms and 500,000 ohms respectively. The voltages of three different frequencies derive from the frequency divider 28 are applied in sequence across the voltage divider, and the voltages developed across the capacitive cell 11 and the resistor 40 are applied to the input of a buffer amplifier 41.

The different voltages developed sequentially across the capacitive cell 11 have voltages proportional to the points on either the curve 25 or the curve 26 (FIG. 2) plotted for the frequencies A, B, and C. The output of the buffer amplifier 41 is connected through a diode 42 to the input of the demultiplexer 30. Outputs of the demultiplexer 30 correspond to the channels of the multiplexer 29 connected to the conductors 31, 32, and 33 from the output of the frequency divider 28 and are connected to respective storage capacitors 43, 44, and 45. When the multiplexer 29 is operated to apply signal with the highest frequency C to the capacitive cell 11, the demultiplexer 30 is operated to apply signal developed across the capacitive cell 11 and rectified by the diode 42 to the capacitor 43, and likewise d-c voltages having amplitudes proportional to the amplitudes of signals for the middle frequency B and the lowest frequency A are applied to the storage capacitors 44 and 45, respectively. The capacitor 43 is connected to the input of an amplifier 46; the capacitor 44 to amplifier 47; and the capacitor 45 to amplifier 49. The respective diodes connected between the outputs and the inputs of the individual amplifiers 46, 47, and 49 compensate for drop in voltage across the diode 42. The outputs of the amplifiers 46 and 47 are connected to the separate inputs of a differential amplifier 48 for deriving at the output of the amplifier 48 a d-c voltage corresponding to the expression $-V_c + K_1V_b$ of the equation described above. The capacitor 45 is connected to the input of an amplifier 49, and the output of the amplifier 49 is connected to one input of a differential amplifier 50. The other input of the differential amplifier 50 is connected to a d-c voltage divider to which d-c voltage is applied according to the constant $K_2$ for deriving at the output of the amplifier 50 the expression $K_2 - K_3V_a$. The outputs of the amplifiers 48 and 50 are applied to separate inputs of the multiplier 51 to provide at its output the d-c voltage having an amplitude proportional to $V_o$ according to the equation shown above. The output of the multiplier 51 is connected through a d-c operational amplifier 52 to the d-c filter comprising the resistors 53 and 54 and the capacitors 55 and 56. The amplifier 52 functions as an isolating amplifier and provides the gain required for operating the d-c indicator over a desired range. The resistor 54 and the capacitor 56 at the output of the filter is connected to a d-c indicator 24. The d-c indicator 24 is conveniently a meter that is calibrated to show percentage of moisture in materials being tested.

Figure 4:
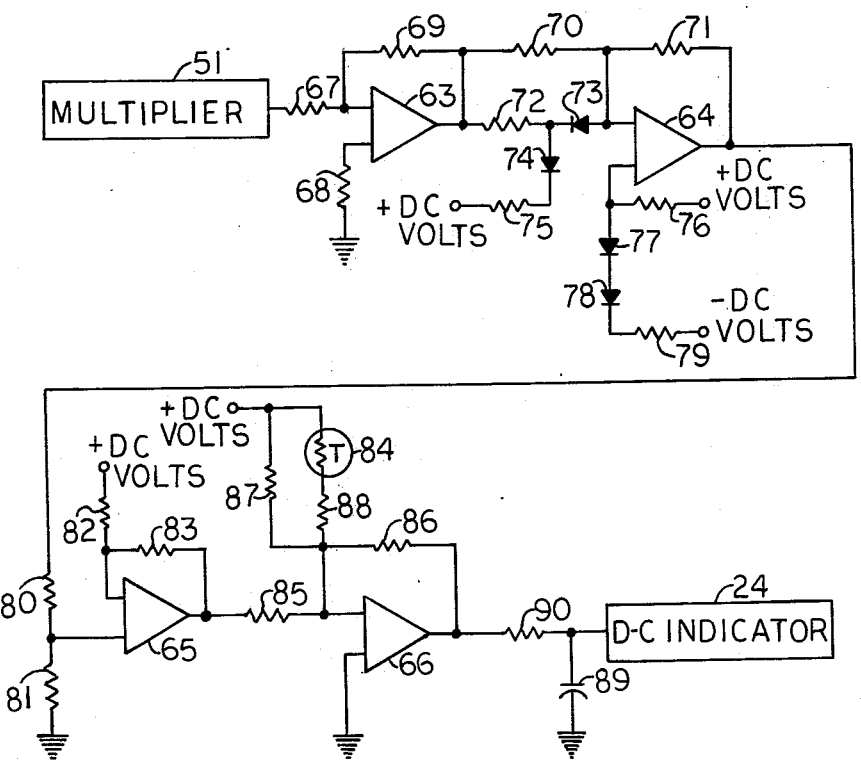
FIG. 4 is a schematic diagram of computer output circuits for temperature compensation and for extending the range of percentages of moisture over a linear scale.

To decrease the effects of the different temperatures of materials being tested and to widen the range of percentages of moisture over which accurate readings can be obtained on the indicator 24, the compensating circuits shown in FIG. 4 are connected between the multiplier 51 and the indicator 24 in place of the simpler circuits shown in FIG. 3. As the temperature of material being tested descreases, the reading on the d-c indicator 24 of FIG. 3 increases even though the moisture content is maintained constant. In effect, when the reading for a certain percentage of moisture is correct at a certain temperature, the reading of the indicator 24, if not corrected, would be too low for a higher temperature and conversely too high for a lower temperature.

Figure 5:
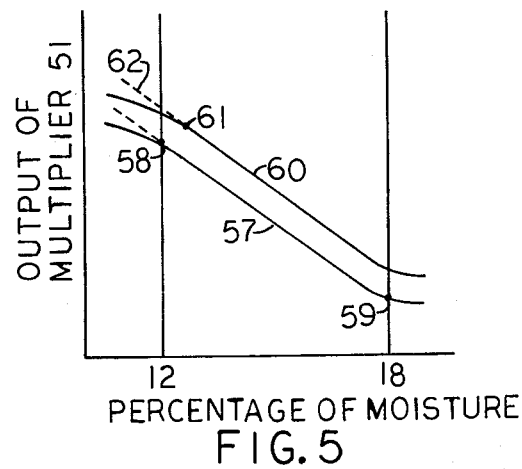
FIG. 5 is a graph to show effects of temperature on the output derived from a capacitive test cell containing grain.

Accurate readings over a minimum range from 12 percent to 18 percent of moisture is required for testing grain. As shown in FIG. 5 this desired range is about the maximum range that can be obtained over the linear part of a curve obtained from plotting output of the multiplier 51 for different percentages of moisture of grain at a fixed temperature. The curve 57 has a linear portion between the output 58 for 12 percent of moisture and the output 59 for 18 percent of moisture. Curve 60 is typical of a curve plotted for the same sample of grain that was used for plotting the curve 57 when the temperature of the grain is lower than it was when curve 57 was plotted.

The portion of the curve 57 at the left of the point 58 for lower percentages of moisture has less slope than the linear portion between the points 58 and 59. On the curve 60, the point 61, corresponding to the point 58 of curve 57, has moved to the right to show a reading for a percentage of moisture greater than the actual 12 percent. To obtain corrected readings at the lower temperature for percentages of moisture down to 12 percent, the curve 60 for percentages of moisture less than that represented by the point 61 must be straightened to obtain the dashed portion 62 at the left of point 61 for the curve 60. Since the output for the lower temperature would then be too great, a correction for temperature is required. Summarizing, the curves must be straightened at the portion near 12 percent of moisture, and a correction must be made for temperature to obtain a range wide enough to extend between 12 percent and 18 percent.

The circuits of FIG. 4 for extending the range include four cascade stages having transistor amplifiers 63, 64, 65 and 66 respectively. The first stage provides gain and inverts the signal in polarity; the second stage inverts the signal back to its original polarity and functions as a break-point amplifier, the amplifier being nonlinear over a range of input voltages having the values for those percentages of moisture near 12 percent where straightening of the curves is required; the third stage inverts the applied signal and offsets the output of the previous stage with respect to zero so that the output of the third stage increases in value with increases in percentages of moisture; and the fourth stage includes a sensing element for sensing the temperature of grain being tested and offsets its output voltage as a function of temperature to compensate for changes in values of input signal with changes in temperature.

In detail, the amplifiers 63–66 are usual transistor operational amplifiers having high input impedance, high gain, and low output impedance. The multiplier 51 is connected through a resistor 67 to one terminal of the amplifier 63 and the other terminal of the amplifier is connected through a resistor 68 to a common conductor or ground. A resistor 69 is connected between the output of the amplifier 63 and its input that is connected to the resistor 67. This stage inverts the polarity of the signal applied from the multiplier 51 and amplifies the signal to a suitable value to be operated on by the succeeding nonlinear stage. Suitable values for the resistor 67, 68, and 69 are 15K (15,000), 15K, and 150K ohms respectively.

The output of the transistor amplifier 63 is connected to the input of the amplifier 64 through a network of resistors and diodes. As the diodes become conductive, the gain of the stage changes from approximately unity to 2.8. A resistor 70 is connected between the output of the amplifier 63 and an input of the amplifier 64, and a feedback resistor 71 is connected between the same input and the output of the amplifier 64. Before the diodes in the input network become conductive, the gain of the stage is generally determined in the usual manner by the feedback resistor 71 and the input resistance determined predominantly by the resistor 70. A resistor 72 and a diode 73 are connected in series across the resistor 70. To determine the value of the signal at which the diodes become conductive, a source of d-c (direct-current) voltage is connected through a resistor 75 and a diode 74 to the point where the resistor 72 and the diode 73 are connected together. As the diode 73 and 74 become conductive for higher levels of signal, the resistor 72 becomes effectively connected in parallel with resistor 70. The input resistance of the amplifier 64 is decreased and its gain is increased to provide greater gain for those input voltages greater than those represented by points 58 and 61 on curves 57 and 60 respectively of FIG. 5. As a result, the linear ranges of the curves 57 and 60 are extended as indicated by the dashed line 62 of curve 60. The other input of the amplifier 64 is connected through a resistor 76 to one terminal of a source of d-c voltage and through serially connected diodes 77, 78 and a resistor 79 to the other terminal of the source d-c voltage. The diodes 72, 77, and 78 provide temperature correction for changing somewhat the point of nonlinear operation for different curves of families of curves corresponding to the curves 57 and 60 of FIG. 5 such that the nonlinear operation occurs at the point of the changing slopes near 12 percent. In a typical tester for measuring the moisture of corn, the values of the resistors of this stage are: resistor 70, 10.25K; resistor 71, 10.2K; resistor 72, 5.6K; resistor 75, 12K; resistor 76, 150.47K; and resistor 79, 140.2K ohms. The source of voltage supplies 15 volts with the polarities indicated in FIG. 4.

The output of the amplifier 64 is connected through the resistor 80 to an input of the amplifier 65, and this input is also connected through a resistor 81 to ground. These resistors supply the required voltage for offsetting the signal from zero such that the output of the amplifier 65 increases in positive value with an increase in the percentage of moisture. The other input terminal of the amplifier 65 is connected through a resistor 82 to a source of d-c voltage that is typically + 15 volts and through a conventional feedback resistor 83 to the output of the amplifier 65. The values of the resistors for this stage are typically: resistors 80 and 81, 11.3K; and resistors 82 and 83, 15K ohms.

The final stage with the amplifier 66 includes a thermistor 84. The thermistor 84 is placed in close contact to the grain being tested and changes the input voltage of this final stage as required to make the output reading on the d-c indicator 24 independent of the temperature of the grain. Before temperature correction, as described above, the output of the multiplier 51 increases as the temperature decreases to give a greater output as if the grain had a somewhat greater percentage of moisture. The thermistor changes the amount of reference voltage applied to the input of this stage sufficiently to compensate for the change in output caused by change in temperature alone.

The output of the amplifier 65 is connected through a resistor 85 to an input of the final amplifier 66, and the other input of the amplifier is connected to ground. A resistor 86 is connected between the output of the amplifier 66 and the input that is connected to the resistor 85. This input is also connected to a resistive network that includes the thermistor 84 for changing the amount by which the input of the amplifier is offset. The network includes a resistor 87 connected between a source of d-c reference voltage and the input of the amplifier 66, and the thermistor 84 and a resistor 88 connected in a series circuit, this series circuit being connected in parallel with the resistor 87. The output of the amplifier is connected through a resistor 90 to the input of the d-c indicator 24, and the filter capacitor 89 is connected between the input of the indicator 24 and ground. Typically, the capacitor 89 has a value of 0.05 microfarad, and the values of the resistors for the final stage are as follows: resistor 85, 10K; resistor 86, 10K; resistor 87, 44.2K; resistor 88, 56K; and resistor 90, 560 ohms.

We claim:

1. An electrical testing system having an output that is a function of the permittivity of materials for determining qualities of the materials, comprising: generating means for exciting periodic electrical waves at a plurality of frequencies, said generating means having signal selective circuits for supplying said waves at respective predetermined ones of said frequencies, a capacitive cell to receive materials for testing, the capacitive impedance of said cell being dependent on the complex permittivity of material placed therein, said signal selective circuits of said generating means connected to said capacitive cell to apply thereto said periodic electrical waves at said predetermined frequencies, output selective circuits connected to said capacitive cell for receiving voltages developed thereacross, said output selective circuits having different output circuits responsive to application of voltages at different ones of said predetermined frequencies for developing different output voltages therein in response to application thereto of said voltages developed across said capacitive cell, the magnitudes of said different output voltages varying systematically in accordance with different impedances of said cell at different ones of said predetermined frequencies, computing means connected to said output circuits of said output selective circuits, said output circuits applying said different output voltages to said computing means, and said computing means being programmed to provide in response to application thereto of said different output voltages an output indicative of the amount of a particular quality associated with the material being tested.

2. An electrical testing system as claimed in claim 1 wherein said generating means includes a source of periodic electrical waves and said signal selective circuits include input multiplexing means connected between said source of periodic electrical waves and said capacitive cell, said input multiplexing means operating in response to application of said periodic electrical waves at a plurality of said frequencies to apply said periodic electrical waves at said predetermined frequencies sequentially and repeatedly to said capacitive cell.

3. An electrical testing system as claimed in claim 2 wherein said output selective circuits include output demultiplexing means synchronized in operation with said input multiplexing means for applying repeatedly said voltages developed across said capacitive cell for each of said plurality of frequencies to said output circuits of said output selective circuits.

4. An electrical testing system as claimed in claim 3 wherein said source of periodic electrical waves is a square wave generator and a frequency divider, said square wave generator having an output connected to said frequency divider, said frequency divider having a plurality of output circuits connected to said multiplexing means, and each of said output circuits of said frequency divider supplying a periodic electrical wave of one of said predetermined frequencies.

5. An electrical testing system as claimed in claim 4 wherein said multiplexing means and said demultiplexing means are each an analog multiplexer, each of said analog multiplexers having a sequence control circuit and a plurality of switching circuits, a common terminal of each of said analog multiplexers connected to all switching circuits of the respective multiplexer, an individual terminal connected to each of said switching circuits, selected ones of said output circuits of said frequency divider connected individually to respective ones of said individual terminals of the switching circuits of said multiplexing means, each of said sequence control circuits having a plurality of input control terminals, other of said output circuits of said frequency divider connected individually to respective ones of said input control terminals of each of said analog multiplexers, said other output circuits applying to said input control terminals said periodic electrical waves of frequencies much lower than the frequencies of the periodic electrical waves applied to said terminals of said switching circuit, said switching circuits of each of said analog multiplexers being operated sequentially in response to application of periodic electrical waves to said input control terminals, said common terminal of said multiplexing means being connected to said capacitive cell for applying said predetermined frequencies thereto, said common terminal of said demultiplexing means connected to said capacitive cell for receiving said voltage developed thereacross, each of said output circuits of said output selective circuits including sampling and holding means, and said individual terminals of said switching circuits of said demultiplexing means connected to respective ones of said sampling and holding means.

6. An electrical testing system as claimed in claim 1 in which said computer has a computer output circuit providing said output indicative of the amount of a particular quality, a d-c indicator, said output changing linearly over a range between separated points on curves for said particular quality and changing a decreasing amount for values outside said range, a break-point amplifier connected between said computer output circuit and said d-c indicator, and said break-point amplifier changing gain in response to change of said output of said computer as said value passes through one of said points to increase the linear range of voltage applied to said d-c indicator.

7. An electrical testing system as claimed in claim 1 in which said computer has a computer output circuit providing said output indicative of the amount of a particular quality, a d-c indicator, an amplifier having a voltage-level control circuit, a thermistor positioned in said capacitive cell to be in thermal contact with material being tested, said thermistor being connected to said voltage level control circuit to control the output of said amplifier according to the temperature of material being tested in said capacitive cell, and said amplifier being connected between said computer output and said d-c indicator.

8. An electrical testing system having an output that is a function of the permittivity of materials for determining the moisture content of the materials comprising: generating means for providing a plurality of electrical signals at different predetermined frequencies, means including a capacitive test cell for receiving material to be tested, circuit means including said capacitive test cell coupled with said generating means for providing a different output signal in response to each of said signals of different predetermined frequencies in accordance with the permittivity of said material received in said test cell, and computing means coupled to said circuit means for receiving said output signals, said computing means including means for combining said different output signals in predetermined proportions for providing a single output signal corresponding to the moisture content of the material being tested.

9. An electrical testing system according to claim 8, wherein said circuit means includes multiplexer means connected between said generating means and said capacitive cell for providing signals at said predetermined frequencies sequentially and repeatedly to said capacitive cell, and demultiplexing means coupled between said capacitive cell and said computing means and synchronized in operation with said multiplexing means for applying sequentially and repeatedly said output signals to said computing means.

10. An electrical testing system according to claim 9, wherein said generating means include means for selecting said different predetermined frequencies and said computing means include means for setting said predetermined proportions for eliminating from said single output signal the effects of substantially all other variables associated with the material being tested except the moisture content thereof.

11. An electrical testing system according to claim 10 further including a thermistor positioned in said capacitive cell to be in thermal contact with the material being tested, said thermistor being connected to said computing means to substantially eliminate the effects upon said single output signal of temperature variations in the material being tested.

12. An electrical testing system as claimed in claim 8, wherein said capacitive cell comprises a cell of the type used in portable moisture testers, including means for receiving a fixed quantity of material to be tested.

13. A testing system according to claim 8 wherein said capacitive cell comprises a cell substantially of the type used in continuous moisture testers, including means for receiving a continuous flow of material therethrough.

14. An electrical testing system according to claim 10, wherein said means for selecting said different predetermined frequencies selects three predetermined frequencies in accordance with the identity of the material being tested, and said setting means included in said computer means sets said predetermined proportions in accordance with the formula $Vo = (-V3 + K1 \cdot V2)(K2 - K3 \cdot V1)$ wherein $Vo$ represents said single output signal of said computer means, $V1$, $V2$ and $V3$ represent said output signals of said circuit means in response to the first, second and third ones of said three predetermined frequencies, respectively, and $K1$, $K2$ and $K3$ are predetermined constants set by said setting means in accordance with the identity of the material being tested.

* * * * *

UNITED STATES PATENT AND TRADEMARK OFFICE
CERTIFICATE OF CORRECTION

PATENT NO. : 4,058,766
DATED : November 15, 1977
INVENTOR(S) : Ronald F. Vogel, Robert R. Boldt, Kevin D. McKee, Roy E. Resh and Paul E. West It is certified that error appears in the above-identified patent and that said Letters Patent are hereby corrected as shown below:

Column 3, line 51, "voltage" should be --voltages--;

Column 8, line 52, after "source" insert --of--;

Column 8, line 60, "resistor 70, 10.25K" should be --resistor 70, 10.2K--.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks